United States Patent
Otto et al.

(10) Patent No.: US 6,183,510 B1
(45) Date of Patent: Feb. 6, 2001

(54) HEART VALVE PROSTHESIS

(76) Inventors: Karl-Heinz Otto, Am Hochbehalter 13; Manfred Wieland, Berchtesgardener Strasse 8, both of Kiel 24146 (DE); Thomas Ebel, Rixenweg 1, Klausdorf/Schwentine, 24147 (DE)

( * ) Notice: Under 35 U.S.C. 154(b), the term of this patent shall be extended for 0 days.

(21) Appl. No.: 09/330,323

(22) Filed: Jun. 11, 1999

(30) Foreign Application Priority Data

Jun. 12, 1998 (DE) .............................................. 198 26 104

(51) Int. Cl.[7] .................................................. A61F 2/24
(52) U.S. Cl. .............................................................. 623/2.22
(58) Field of Search ................................ 623/2.22, 2.23, 623/2.24, 2.25, 2.26, 2.27

(56) References Cited

U.S. PATENT DOCUMENTS

| | | | | |
|---|---|---|---|---|
| 4,373,216 | * | 2/1983 | Klawitter | 623/2.22 |
| 4,863,459 | * | 9/1989 | Olin | 623/2.22 |
| 4,872,875 | * | 10/1989 | Hwang | 623/2.22 |
| 4,935,030 | * | 6/1990 | Alonso | 623/2.22 |

* cited by examiner

*Primary Examiner*—Bruce Snow
(74) *Attorney, Agent, or Firm*—Larson & Larson, P.A.; James E. Larson

(57) ABSTRACT

A heart valve prosthesis with a valve ring and at least one substantially elongated wing valve pivotally mounted about an axis located in the plane of the valve ring, in which the bearings of the wing valve or valves are in each case formed by a swivel pin, defining the swivel axis and fixed to the valve ring, a groove constructed in the wing valve and extending therethrough transversely to the axis and whose width corresponds to the diameter and whose depth corresponds to the length of the swivel pin, a first guide pin fixed to the valve ring, a first, convex slide cam constructed on the wing valve and which cooperates with the first guide pin, a second guide pin fixed to the valve ring and a second, convex slide cam constructed on the wing valve and which cooperates with the second guide pin, the spacing from one another of the two slide cams measured over the imaginary connecting line between the centers of the guide pins, in each position of the wing valve, corresponds to the internal, mutual spacing of the two guide pins.

7 Claims, 1 Drawing Sheet

HEART VALVE PROSTHESIS

PRIOR APPLICATIONS

This application is a U.S. application which bases foreign priority on German patent application number 198 26 104.7, filed Jun. 12, 1998 (Jun. 12, 1998).

BACKGROUND OF THE INVENTION

1. Field of the Invention

The invention relates to a heart valve prosthesis to be used as a replacement for natural heart valves and which has a valve ring and at least one substantially elongated wing valve mounted on the valve ring and pivotable about an axis located in the valve ring plane.

2. Description of the Prior Art

DE 37 01 755 C1, U.S. Pat. Nos. 5,192,309, 4,328,592 and DE 196 33 346 C1 disclose in connection with heart valve prostheses to so construct the bearings of the wing valves that they are "thoroughly washed" by the bloodstream. In DE 37 01 755 C1 this takes place through special inflow and outflow funnels following the bearings, in U.S. Pat. Nos. 5,192,309 and 4,328,592 through longitudinal grooves on the inside of the valve ring. In DE 196 33 346 C1 journals projecting into elongated holes in the wing valves are provided.

WO 97 05 834 and U.S. Pat. No. 4,935,030 disclose slideways for the wing valves.

SUMMARY OF THE INVENTION

The problem of the invention is to provide a heart valve prosthesis, whose bearings, around all of whose areas flows blood, ensure a precise guidance of the heart valve.

The proposed bearing construction with a groove receiving the swivel pin permits a constant rinsing of all areas of the bearing by the bloodstream and in conjunction with the slide cams the guide pins ensure a forced guidance of the valve.

The invention may be best understood by those having ordinary skill in the art by reference to the following detailed description when considered in conjunction with the accompanying drawings in which:

DETAILED DESCRIPTION OF THE PREFERRED EMBODIMENT

Figure 1:
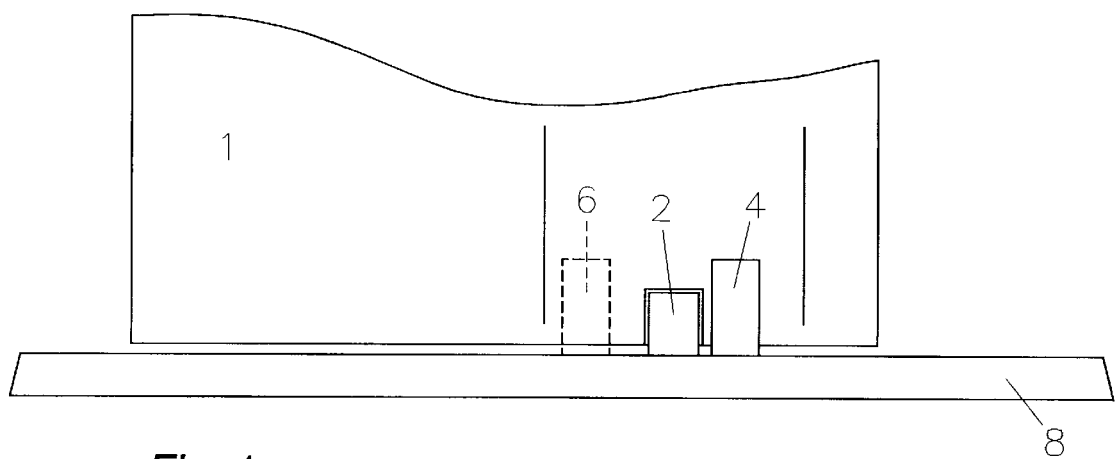
FIG. 1 The bearing in a diagrammatic development of a plan view on the ring plane.

The heart valve prosthesis comprises a valve ring 8 and at least one substantially elongated wing valve 1 pivotably mounted about an axis located in the plane of the valve ring 8.

The wing valve 1 is fixed by means of in each case two bearings to the valve ring 8, whereof only one is shown in the drawings.

The bearing comprises a swivel pin 2 fixed to the valve ring 8, shown in a development in FIG. 1 and which together with the corresponding swivel pin of the other bearing of the particular wing valve 1 defines the swivel axis thereof. In the wing valve 1 is formed a groove 3 extending therethrough transversely to the axis and whose width corresponds to the diameter and whose depth corresponds to the length of the swivel pin 2.

To the valve ring 8 is fixed a first guide pin 4, which cooperates with a first, convex slide cam 5 constructed on the wing valve 1. A second guide pin 6 fixed to the valve ring 8 cooperates with a second, convex slide cam 7 constructed on the wing valve 1.

The internal spacing of the two guide pins 4, 6 with respect to one another corresponds to the spacing of the two slide cams 5, 7 with respect to one another measured over the centre of the swivel pin 2. The two guide pins 4, 6 are longer than the swivel pin 2.

Figure 2:
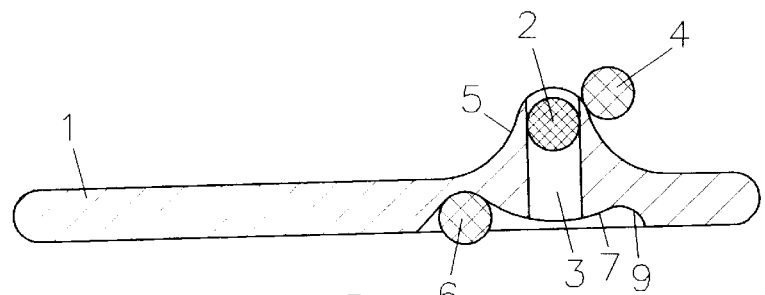
FIG. 2 A representation, sectioned in the area of the bearing, of the valve wing in the closed position.
Figure 3:
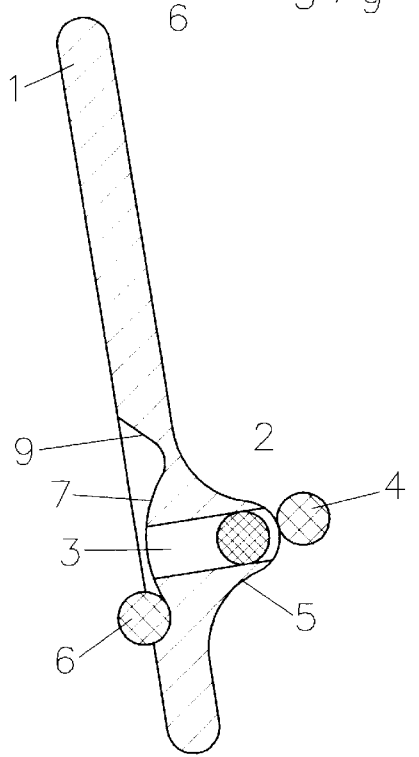
FIG. 3 A representation of the valve wing, sectioned in the area of the bearing, in the open position.

To the convex, second slide cam 7 axe connected concave contact sections 9, on which engage the wing valve 1 passing between the guide pins 4, 6 in its end positions, shown in FIGS. 2 and 3, on the second guide pin 6.

No drawing shows a construction in which one or both guide pins 4, 6 are wholly or partly made from an elastic material. This construction has the advantage that the striking of the wing valves on the pins 4, 6 is damped. A partial or complete construction of the guide pins from an elastomer can also be used for pretensioning the wing valve in its end positions in the direction of the following movement, which has a favourable effect on the speed of the closing and opening behaviour.

It is obvious that the dimensioning of the individual, cooperating elements is chosen in such a way that there is an adequately large clearance between them.

What is claimed is:

1. A heart valve prosthesis having a valve ring and at least one substantially elongated wing valve pivotally mounted about an axis located in the plane of the valve ring, characterized in that bearings of the at least one substantially elongated wing valve include:

a) a swivel pin defining a swivel axis and fixed to the valve ring;

b) a groove constructed in the wing valve and extending therethrough transversely to the axis and whose width corresponds to a diameter and whose depth corresponds to a length of the swivel pin;

c) a first guide pin fixed to the valve ring;

d) a first convex slide cam constructed on the wing valve cooperating with the first guide pin;

e) a second guide pin fixed to the valve ring; and f) a second convex slide cam constructed on the wing valve cooperating with the second guide pin such that a spacing of the two slide cams from one another in each wing valve position measured over a connecting line between centers of the guide pins, corresponds to an internal spacing of the two guide pins with respect to one another.

2. A heart valve prosthesis according to claim 1 wherein the two guide pins are longer than the swivel pin.

3. A heart valve prosthesis according to claim 1 further comprising concave contact sections connecting on either side to the convex second slide cam.

4. A heart valve prosthesis according to claim 1 wherein the first guide pin is wholly made from an elastic material.

5. A heart valve prosthesis according to claim 1 wherein the first guide pin is partially made from an elastic material.

6. A heart valve prosthesis according to claim 1 wherein the second guide pin is wholly made from an elastic material.

7. A heart valve prosthesis according to claim 1 wherein the second guide pin is partially made from an elastic material.

* * * * *